(12) United States Patent
Bonde et al.

(10) Patent No.: US 10,293,090 B2
(45) Date of Patent: May 21, 2019

(54) PERCUTANEOUS DEVICE AND METHOD FOR PROMOTING MOVEMENT OF A BODILY FLUID

(71) Applicant: Yale University, New Haven, CT (US)

(72) Inventors: Pramod Bonde, Woodbridge, CT (US); Brian Letzen, Orange, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/695,750

(22) Filed: Apr. 24, 2015

(65) Prior Publication Data

US 2015/0306291 A1    Oct. 29, 2015

Related U.S. Application Data

(60) Provisional application No. 61/984,345, filed on Apr. 25, 2014.

(51) Int. Cl.
*A61M 1/10* (2006.01)
*A61M 1/12* (2006.01)

(52) U.S. Cl.
CPC ............ *A61M 1/122* (2014.02); *A61M 1/101* (2013.01); *A61M 1/1015* (2014.02); *A61M 1/1031* (2014.02); *A61M 1/125* (2014.02); *A61M 2205/0266* (2013.01)

(58) Field of Classification Search
CPC .... A61M 1/1012; A61M 1/122; A61M 1/125; A61M 1/1015; A61M 1/1031; A61M 2205/0266
See application file for complete search history.

(56) References Cited

U.S. PATENT DOCUMENTS

| | | | |
|---|---|---|---|
| 4,335,711 A * | 6/1982 | Olson | A61B 90/00 128/899 |
| 4,625,712 A | 12/1986 | Wampler | |
| 5,376,114 A * | 12/1994 | Jarvik | A61M 1/102 128/898 |
| 5,749,855 A | 5/1998 | Reitan | |
| 5,755,784 A | 5/1998 | Jarvik | |
| 5,964,694 A | 10/1999 | Siess et al. | |
| 6,136,025 A * | 10/2000 | Barbut | A61F 2/90 604/530 |
| 6,176,822 B1 | 1/2001 | Nix et al. | |
| 6,514,226 B1 | 2/2003 | Levin et al. | |
| 6,981,942 B2 | 1/2006 | Khaw et al. | |

(Continued)

OTHER PUBLICATIONS

Definition of contiguous in US English by Oxford Dictionaries. https://en.oxforddictionaries.com/definition/us/contiguous. Accessed Nov. 20, 2017.*

(Continued)

*Primary Examiner* — Adam Marcetich
(74) *Attorney, Agent, or Firm* — Riverside Law LLP

(57) ABSTRACT

The present invention provides a minimally-invasive percutaneous device that can be positioned within the body of a subject to aid in the movement or pumping of a bodily fluid. In one embodiment, the device comprises a plurality of pump units configured to transform from a first compressed configuration where the pump units are organized in a serial arrangement into a second expanded configuration where the pump units are reorganized into a parallel arrangement.

12 Claims, 16 Drawing Sheets

(56) References Cited

U.S. PATENT DOCUMENTS

| | | | |
|---|---|---|---|
| 7,022,100 B1 | 4/2006 | Aboul-Hosn et al. | |
| 7,144,364 B2 | 12/2006 | Barbut et al. | |
| 7,993,259 B2 | 8/2011 | Kang et al. | |
| 8,376,707 B2 | 2/2013 | McBride et al. | |
| 8,409,276 B2 | 4/2013 | Wampler | |
| 8,454,549 B2 | 6/2013 | Zafirelis et al. | |
| 8,485,961 B2 | 7/2013 | Campbell et al. | |
| 8,535,211 B2 | 9/2013 | Campbell et al. | |
| 8,545,380 B2 | 10/2013 | Farnan et al. | |
| 8,550,973 B2 | 10/2013 | Magovern et al. | |
| 2003/0127090 A1* | 7/2003 | Gifford | A61M 16/0057 128/200.24 |
| 2003/0233143 A1* | 12/2003 | Gharib | A61F 2/86 623/3.1 |
| 2004/0024285 A1* | 2/2004 | Muckter | A61M 1/101 600/16 |
| 2005/0043790 A1* | 2/2005 | Seguin | A61F 2/2403 623/2.18 |
| 2006/0036127 A1* | 2/2006 | Delgado, III | A61M 1/1072 600/16 |
| 2006/0155158 A1* | 7/2006 | Aboul-Hosn | A61M 1/12 600/16 |
| 2006/0178552 A1* | 8/2006 | Gross | A61F 2/24 600/16 |
| 2007/0100435 A1* | 5/2007 | Case | A61F 2/2418 623/1.24 |
| 2007/0239265 A1* | 10/2007 | Birdsall | A61F 2/2412 623/1.26 |
| 2007/0250146 A1* | 10/2007 | Cully | A61F 2/07 623/1.2 |
| 2008/0167614 A1* | 7/2008 | Tolkowsky | A61M 16/04 604/131 |
| 2009/0107511 A1* | 4/2009 | Gross | A61M 16/0066 128/207.15 |
| 2010/0076247 A1* | 3/2010 | Zilbershlag | A61M 1/101 600/17 |
| 2011/0152999 A1* | 6/2011 | Hastings | A61M 1/1029 623/1.15 |
| 2011/0257462 A1* | 10/2011 | Rodefeld | A61F 2/01 600/16 |
| 2013/0138205 A1* | 5/2013 | Kushwaha | A61M 1/101 623/1.26 |
| 2013/0274648 A1* | 10/2013 | Weinberger | A61M 1/3655 604/9 |
| 2013/0294189 A1* | 11/2013 | Myrick | B01F 3/0446 366/162.4 |
| 2013/0310630 A1 | 11/2013 | Smith et al. | |
| 2014/0051908 A1* | 2/2014 | Khanal | A61M 1/1024 600/17 |
| 2014/0128659 A1* | 5/2014 | Heuring | A61M 1/101 600/16 |
| 2014/0171889 A1* | 6/2014 | Hopman | A61M 1/0011 604/321 |
| 2014/0275727 A1 | 9/2014 | Bonde et al. | |
| 2015/0141739 A1* | 5/2015 | Hsu | A61M 1/1024 600/16 |
| 2015/0142100 A1* | 5/2015 | Morriss | A61F 2/2418 623/2.4 |

OTHER PUBLICATIONS

Definition of Contiguous by Merriam-Webster. https://www.merriam-webster.com/dictionary/contiguous. Accessed Nov. 20, 2017.*

* cited by examiner

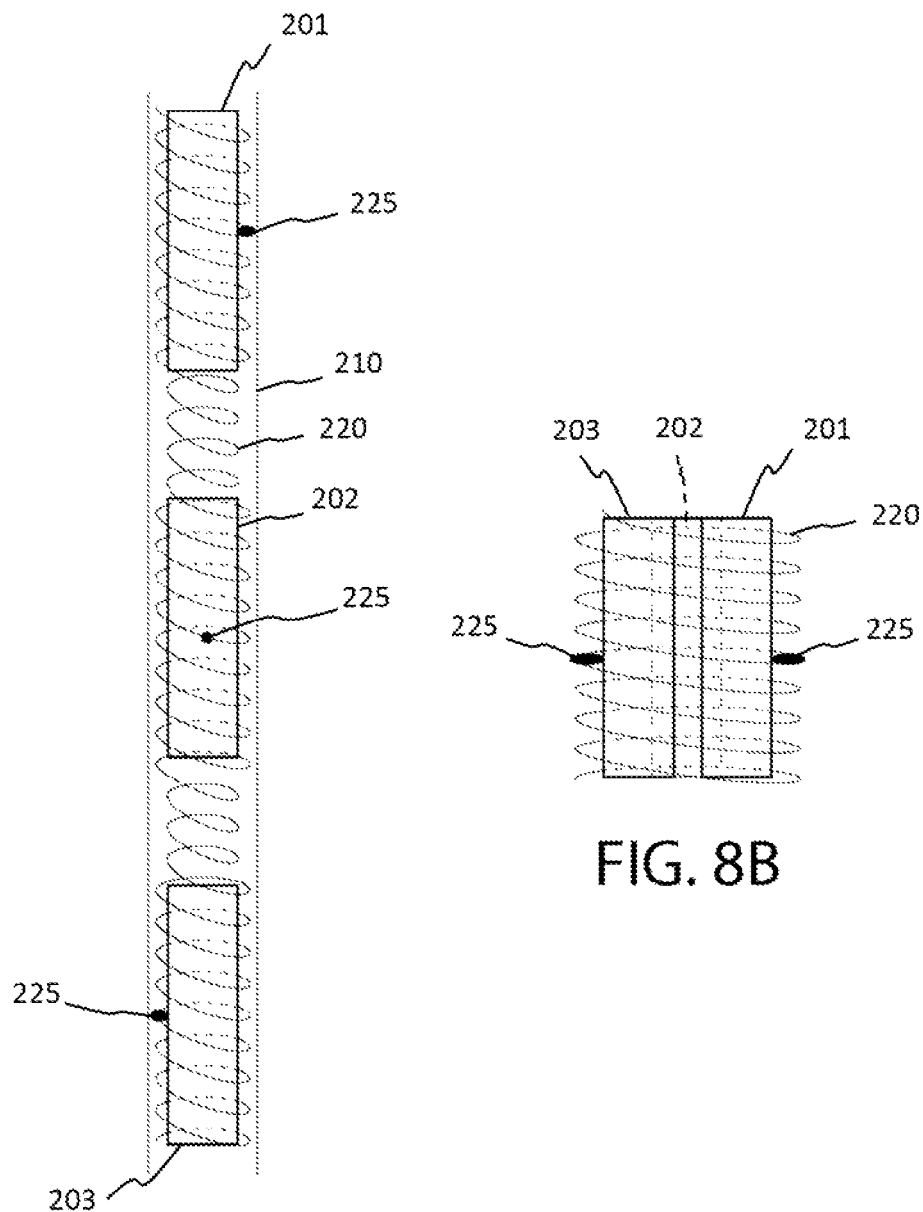

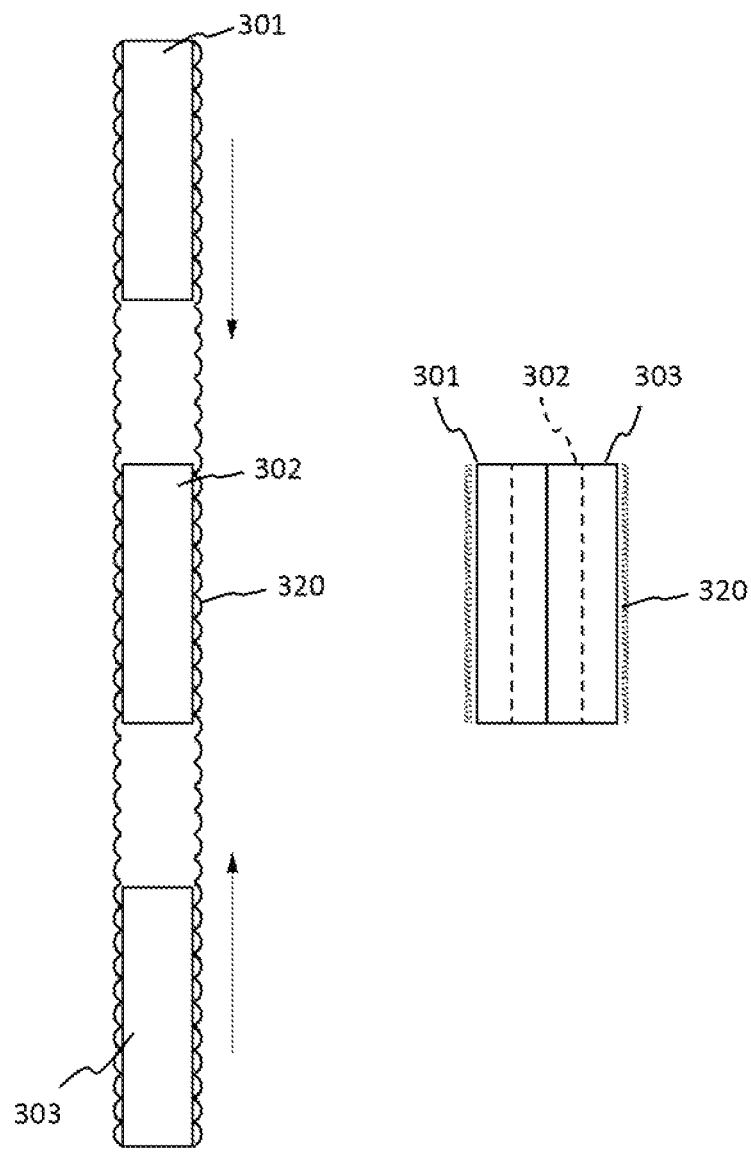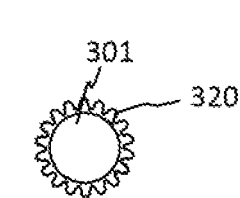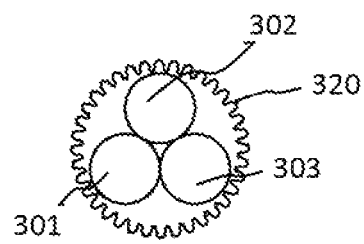
FIG. 9A  FIG. 9B
FIG. 9C  FIG. 9D

PERCUTANEOUS DEVICE AND METHOD FOR PROMOTING MOVEMENT OF A BODILY FLUID

CROSS-REFERENCE TO RELATED APPLICATIONS

The application claims priority to U.S. provisional application No. 61/984,345 filed on Apr. 25, 2014, incorporated herein by reference in its entirety.

BACKGROUND OF THE INVENTION

Congestive heart failure (CHF) is a condition where the heart is unable to pump enough blood to meet the demands of the body. There are approximately 5.8 million current patients with CHF in the United States, and an estimated 500,000 new patients emerge each year. Advancements in medical and surgical therapies have significantly improved survival and quality of life, but advanced heart failure patients still experience a mortality rate of 50-75% per year. The standard for treating these advanced heart failure patients is cardiac transplantation, but this is limited to a small number of patients (approximately 2,000 per year) due to donor shortage. As such, left ventricular assist devices (LVADs) have increased in utilization to support this demand by providing either "bridge to transplantation" or "destination therapy" roles. As LVAD designs have improved over the years, they have resulted in significantly decreased mortality and improved quality of life in comparison with optimal medical management. While great advances have been made, LVAD patients still suffer from several procedural and long-term complications directly related to these devices.

The invasiveness of the LVAD implantation procedure itself confers its own potential complications, including significant hemorrhage. The procedure involves an open heart surgery and the institution of cardiopulmonary bypass while the LVAD is sutured to the apex of the heart and the ascending aorta. Since these patients are especially at risk for hemodynamic decompensation, reducing the invasiveness of the procedure is important in preventing instability and death.

One possible solution to significantly minimize the invasiveness would be the utilization of percutaneous endovascular techniques, where a miniaturized device could be inserted into a blood vessel near the skin and guided to the heart using real-time x-ray images, avoiding the need for open heart surgery. The Impella 2.5 (Abiomed) is a temporary left heart pump that can be inserted through the femoral artery and guided to the left ventricle in this manner. It is approved for providing short-term partial circulatory support up to 6 hours. While useful for short-term application, its inherent design prevents its application for long-term implantation equivalent to current LVADs. The Impella 2.5 includes a motor that is attached to an impeller and lacks a complete seal so that the shaft of the motor is able to spin. Thus, in addition to the power line exiting the femoral artery, an additional percutaneous line containing glucose purge fluid must be connected to the motor to overcome the pressure of blood from entering the motor unit.

Additionally, percutaneous LVADs are limited by the small diameter of the vessel used for introduction. For instance, the percutaneous Impella 2.5 requires extremely small impeller blades and is thus limited to a flow rate of 2.5 L/min. Moreover, these small designs require the motor to spin at a high speed, resulting in increased heating of the motor which can create the need for a cooling solution if used over the long-term. Some efforts, such as the Percutaneous Heart pump from Thoratec, have employed elastic impellers to attempt to overcome this small vessel limitation. However, these flexible materials may not provide sufficient durability for long-term use if they are constantly deflecting blood at 10,000-30,000 revolutions per minute as compared to durable materials found in traditional impellers, made of materials such as titanium.

Thus, there is a need in the art for devices, systems and methods that provide long-term LVAD function while reducing the invasiveness and dangerous risks of the current implantation procedure. The present invention satisfies this unmet need.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A shows a delivery sheath surrounding individual pumps, the device in a compressed state and pumps in a series configuration as the delivery sheath advances towards the aortic arch. FIG. 1B shows the device expanded in a relaxed state and pumps reorganized into a parallel configuration after the device is deployed from the sheath and positioned at the implantation site. FIG. 1C shows a delivery catheter inserted into the patient's femoral artery, advanced to a target delivery zone in the aorta, and deployment of the device at the implantation site.

FIG. 7A shows the magnets and the impeller, and FIG. 7B is a close-up of the drive shaft magnet interfacing with the impeller magnet.

FIGS. 8A and 8B are side views of an exemplary mechanism for connection of the pump units to a frame that allows for rearrangement of the pump units into the parallel arrangement upon expansion of the frame. FIG. 8A shows the pump units in a series arrangement while the frame is in a compressed state within a sheath, and FIG. 8B shows the pump units in a parallel arrangement while the frame is in a relaxed state outside the sheath.

FIGS. 9A-9D depict an exemplary configuration of a frame suitable to transform the device from its serial to parallel configuration. FIGS. 9A and 9B are side views of the frame, and FIGS. 9C and 9D are top views of the frame.

FIG. 10A shows the frame in a compressed state and FIG. 10B shows the frame in a relaxed state.

FIG. 11A shows the frame in a compressed state and FIG. 11B shows the frame in a relaxed state. An alternate embodiment is shown in the side views of FIGS. 11C and 11D.

FIG. 12A is a side view of the frame in a compressed state, FIG. 12B is a side view of the frame in a relaxed state, and FIG. 12C is a top view of the frame in a relaxed state.

DETAILED DESCRIPTION

Figure 1A:
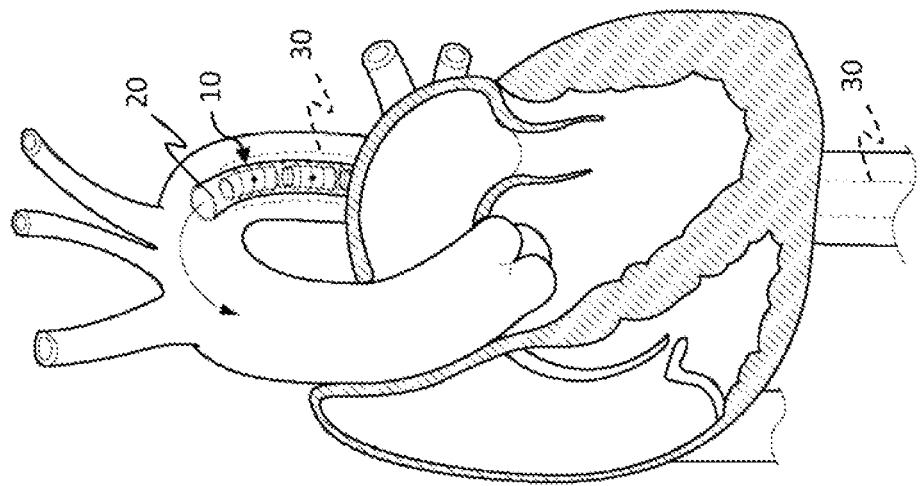
FIGS. 1A-1C are diagrams of the device and an insertion method according to an exemplary embodiment of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present invention includes minimally-invasive percutaneous devices and systems that can be positioned within the body of a subject to aid in the movement or pumping of a bodily fluid. For example, in certain instances, the devices and systems provide for movement of blood, urine, sweat, air, and the like. In a particular embodiment, the devices aid or replace ventricle function of the heart by moving blood out of either the right or left ventricle into the pulmonary or systemic circulation, respectively.

In one embodiment, the invention provides a LVAD configured for minimally-invasive percutaneous delivery to the implantation site. The device is capable of providing long-term support with overall hemodynamic performance and durability comparable to current conventional long-term LVADs, which require a risky open heart surgery and bypass for implantation.

In one embodiment, the device of the invention comprises a plurality of pump units, which in a first conformation are arranged in series for percutaneous delivery. The device is capable of transforming into a second conformation at the desired implantation site where the pump units are reorganized into a parallel additive arrangement (see for example FIG. 1). The pump units are constructed of standard, durable materials allowing for long-term use. Further, the parallel arrangement of pump units at the implantation site allows for reduced heating and for the presence of backup pumps in the case of single motor failure.

In one embodiment, the device of the invention comprises a single miniature pump and a surrounding shell, which amplifies the flow rate produced by the single pump. The device may be delivered in a first compressed configuration, where the shell is compressed to the pump surface, and transformed into a second expanded configuration, where the shell expands to create a fluid filled space between the pump surface and shell (see for example FIG. 13-14).

Figure 1B:
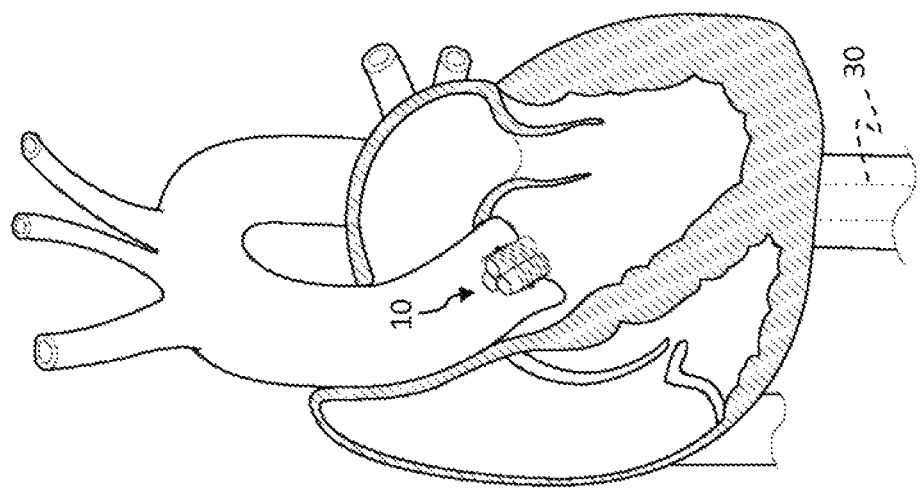
Figure 1C:
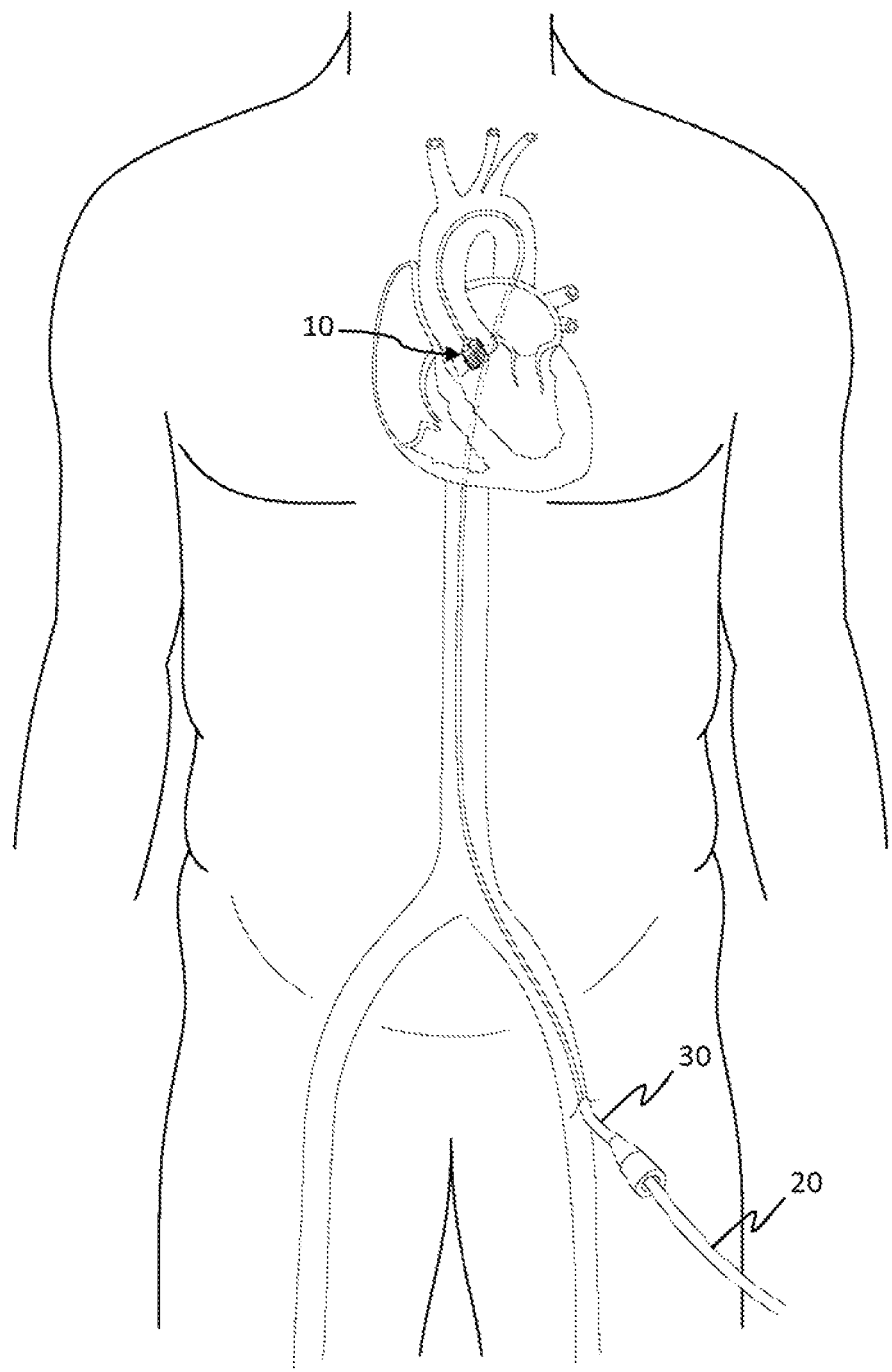

As depicted in FIGS. 1A-1C, the device 10 of an embodiment of the invention comprises a plurality of pump units housed and connected to a flexible frame (details provided throughout the exemplary embodiments). The frame is capable of altering its shape depending upon external forces exerted onto the frame by surrounding body tissues or in certain embodiments, a shape-holding sheath 20 and delivery catheter 30. In certain embodiments, the frame is loaded into the sheath 20, and a delivery catheter 30 is coaxially loaded over the sheath 20 for easy advancement to the treatment area within the body. The delivery catheter 30 can be advanced to areas in or near the heart, such as the aorta. As illustrated in FIG. 1C, the delivery sheath 30 can be introduced to the patient's vasculature from an artery such as the femoral artery. When the sheath 20 is loaded within a separate delivery catheter 30, the sheath 20 can move independently of the delivery catheter 30, and can be advanced at least partially from the tip of the delivery catheter 30 for deploying the device 10 to the target implantation area. In certain embodiments, the frame is loaded directly into the delivery catheter, and the delivery catheter 30 acts as both the compressive sheath for maintaining the frame and the device 10 in the series compressive state, and as the delivery mechanism for advancing the device 10 from the insertion site to the target treatment site. For example, in one embodiment, when the device is being delivered through a blood vessel, the frame has an elongated narrow shape having a small diameter. The elongated narrow shape of the frame thus promotes the first compressed conformation of the device, where the plurality of pump units are arranged in series. In one embodiment, upon entering a wider caliber vessel or other body cavity, the frame expands into a shape having a larger diameter. In certain embodiments, frame expansion is based on temperature-dependent properties of the material of the frame. The expansion of the frame promotes the second expanded conformation of the device, where the plurality of pumps are arranged in parallel. Thus, in certain embodiments, the device exists in a compressed, loaded or biased state during delivery, and in a relaxed state during operation and at the site of implantation.

The parallel arrangement in the expanded conformation provides for durability of each pump unit, since each pump is small enough to be made from sturdy durable materials such as titanium and other medical grade alloys known in the art. Further, parallel arrangement of pump units allow for reduced motor heating, since each individual motor requires a lower operating speed. The parallel arrangement in the expanded conformation allows additive functionality of the pump units as well as providing for backup units in the event that one of the plurality of units fails.

Figure 2:
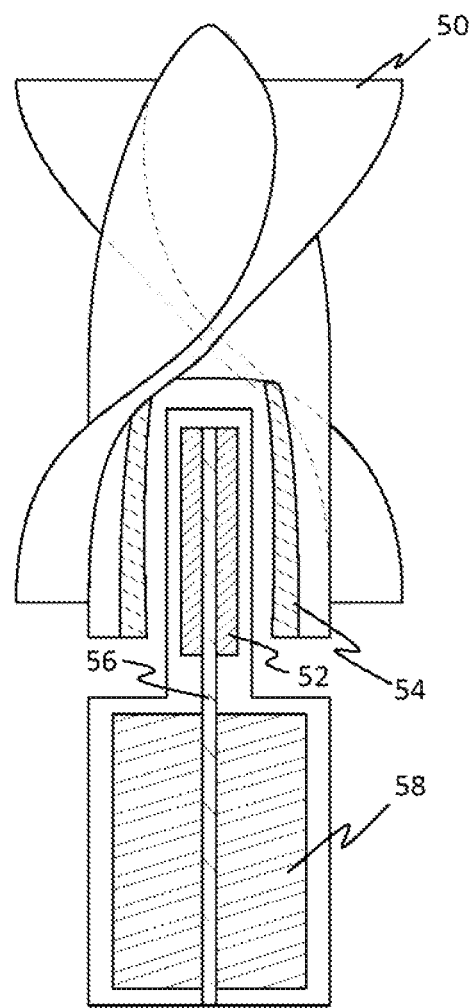
FIG. 2 is a side partial cutaway view depicting the components of an exemplary pump unit.
Figure 3:
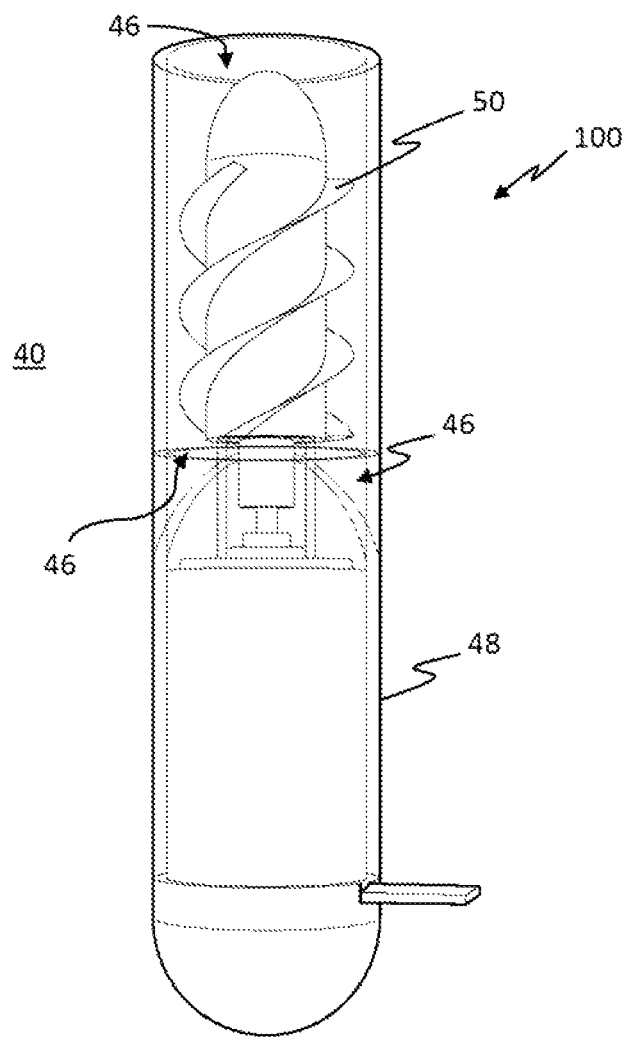
FIG. 3 is a side view of an exemplary pump unit.

As depicted in the exemplary embodiment of FIG. 2 and FIG. 3 each pump unit 100 comprises a pump housing 48 which houses a sealed motor 58 and an impeller 50. The motor 58 drives the drive shaft 56, which drives the drive shaft magnets 52, and in turn drives the impeller magnets 54 for turning the impeller 50. Other medical grade motor drive systems known in the can be utilized for turning the impeller or pumping fluid. Each pump unit has dimensions that allow for its insertion and guidance through a blood vessel. For example, in certain embodiments, each pump unit is cylindrically shaped with a diameter of about 1-30 mm. In one embodiment, each pump unit is cylindrically shaped with a diameter of about 5-20 mm. In one embodiment, each pump unit has a length of about 10-50 mm.

The motor can consistent of any apparatus capable of fitting through the blood vessel while providing sufficient rotational energy and torque. For example, one embodiment consists of a brushless dc motor, while another embodiment consists of a brushed dc motor. The motor can be controlled to provide pulsatile or continuous flow, at either a predefined speed or at a dynamic speed in response to the input from various types of sensors.

In certain embodiments, the motor is connected to a drive shaft which is coupled to the impeller. In one embodiment, the motor and drive shaft are completely sealed from fluid, which eliminates the need for a purge fluid line present in current temporary percutaneous devices to keep blood from entering the motor. The impeller is positioned at the distal end of the pump unit and is outside of the sealed region of the pump, thus allowing the impeller to come into contact with the fluid.

According to one embodiment, the pump housing surrounds the sealed motor, drive shaft and impeller. The housing may be of any suitable geometry, including, cylindrical, rectangular, and the like. The housing may be made from any suitable biocompatible material, including, but not limited to titanium, stainless steel, polyether ether ketone, polyurethane, or graphene. In one embodiment, the pump housing comprises one or more openings which allow for the fluid to enter the interior of the pump unit. For example, in FIG. 3, at least three openings 46 are shown for allowing fluid communication between interior portions of the pump unit 100 including the impeller 50, and the exterior 40 of the pump unit. Thus, when the pump unit 100 is implanted in a vessel, the pump unit 100 can pump nearby blood through the openings 46 via the impeller 50 at the location of implantation. In one embodiment, the pump housing comprises one or more openings which allow for fluid to escape the unit. Thus, fluid enters through at least one opening in the housing and comes into contact with the impeller. Upon rotation of the impeller, as driven by the coupled drive shaft, the fluid is pumped out of the unit via at least one opening of the housing. In one embodiment, the fluid enters through one or more openings positioned at or near the drive shaft and exits via an opening positioned at the distal end of the pump. In another embodiment, the fluid enters through an opening positioned at the distal end of the pump and exits via one or more openings positioned at or near the drive shaft.

In one embodiment, each pump produces a flow rate of about 1 mL/min to about 5 L/min. In one embodiment, the device collectively produces a flow rate of about 1 mL/min to about 10 L/min.

Figure 4A:
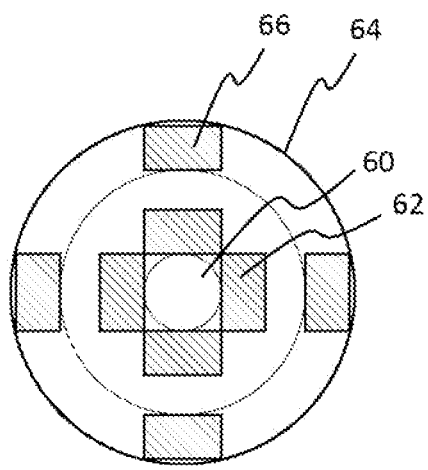
FIGS. 4A-4D are a set of diagrams depicting various exemplary configurations of drive shaft magnets interfaced with impeller magnets.
Figure 4B:
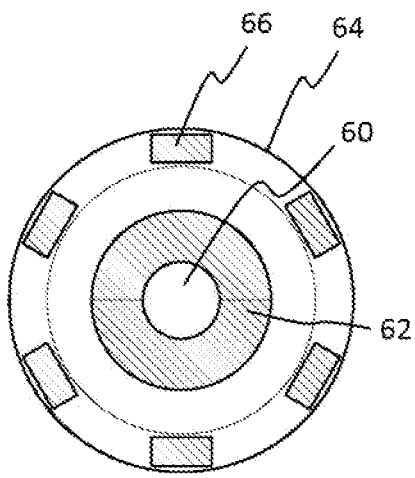
Figure 4C:
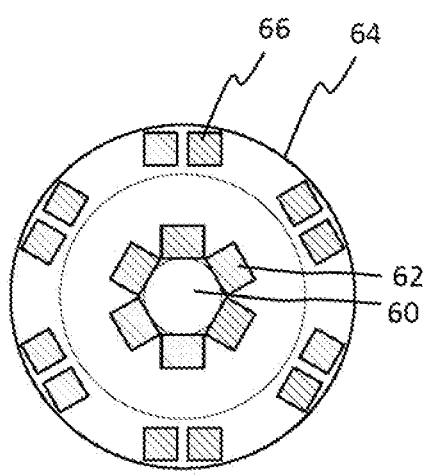
Figure 4D:
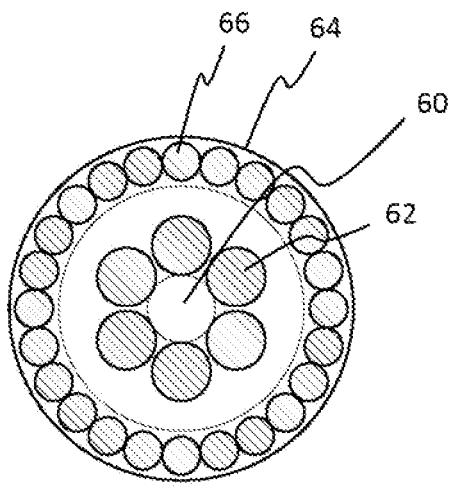

In one embodiment, the impeller is bearingless, allowing for the free-spinning of the impeller. In one embodiment, the impeller is magnetically coupled to the drive shaft. FIGS. 4A-4D depict several exemplary arrangements of drive shaft magnets 62, positioned on or in the drive shaft 60, coupled to impeller magnets 66, positioned on or in the impeller 64. The drive shaft magnets 62 may have rectangular (FIGS. 4A and 4C), curved or annularly surrounding (FIG. 4B) or circular (FIG. 4D). The impeller magnets 66 can be generally spaced apart (FIGS. 4A and 4B), in sets (FIG. 4C) or fairly continuous (FIG. 4D). The magnets 62, 66 generally form a radial pattern about the axis of the drive shaft 60. In one embodiment, the drive shaft comprises one or more drive shaft magnets positioned on or in the drive shaft. In one embodiment, the pump unit comprises a drive shaft enclosure that surrounds the drive shaft. In certain embodiments, the drive shaft magnets are positioned on or in the drive shaft enclosure. The impeller comprises a drive shaft mating region positioned at the proximal end of the impeller, which engages the drive shaft and drive shaft enclosure. The drive shaft and drive shaft mating region of the impeller may have any suitable geometry that allows for the stable coupling of the impeller to the drive shaft. For example, the drive shaft may be cylindrical, rectangular, polygonal, or irregular shaped geometry, while the drive shaft mating region may be a cylindrical, rectangular, polygonal, or irregular shaped cavity, respectively. In one embodiment, the impeller comprises one or more impeller magnets which couple to the one or more drive shaft magnets. Thus, as the drive shaft turns, the magnetic coupling between the drive shaft magnets and the impeller magnets allows the impeller to turn. The magnetic coupling obviates the need for a dynamic rotary seal around the drive shaft.

There are numerous types of magnets that may be utilized in the device of the present invention. For example, the drive shaft magnets and impeller magnets may be any type of magnet including, but not limited to, alternating magnets, continuous magnets, axially polarized magnets, radially polarized magnets. The magnets may be of any suitable strength. Further, any number of drive shaft magnets and impeller magnets may be used that provide efficient magnetic coupling of the impeller to the drive shaft. In certain embodiments, the ratio of drive shaft magnets to impeller magnets ranges from about 1:1 to about 1:10.

The magnets may also be of any suitable shape, including, but not limited to, spherical, cylindrical, rectangular, polygonal, arc-shaped, ring-shaped, and the like. FIGS. 4A-4D depict just a sample of exemplary arrangements of drive shaft magnets 62, positioned on or in the drive shaft 60, coupled to impeller magnets 66, positioned on or in the impeller 64.

Figure 5A:
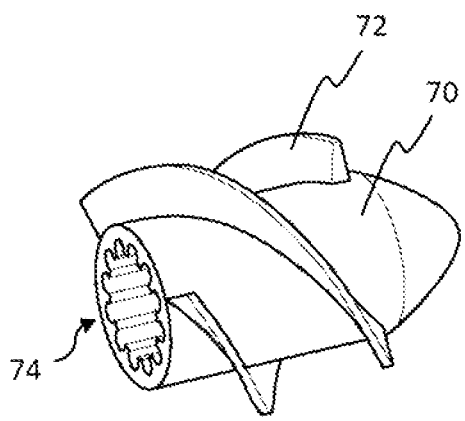
FIGS. 5A-5C are perspective views of embodiments of exemplary impellers. The blades of the impeller may be positioned at the proximal end of the impeller (FIG. 5A), the distal end of the impeller (FIG. 5B), or throughout the entire length of the impeller (FIG. 5C).
Figure 5B:
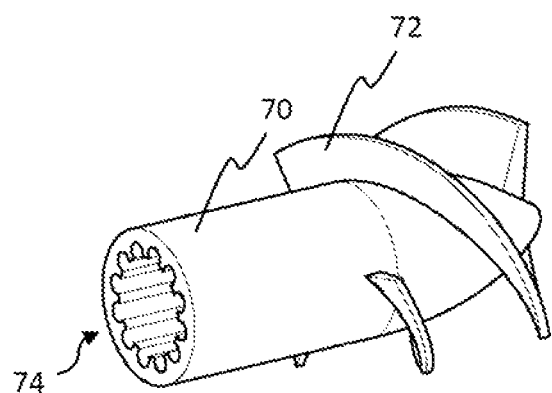
Figure 5C:
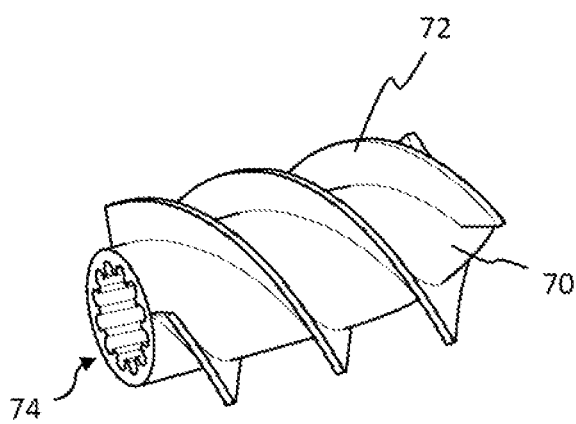

As shown in the exemplary embodiments of impellers of FIGS. 5A-5C, the impeller of the device comprises an impeller body 70, one or more impeller blades 72 positioned along the surface of the impeller body 70, and a drive shaft mating region 74 positioned at the proximal end of the impeller. The impeller may be made of any suitable material, including, but not limited to titanium, stainless steel, polyether ether ketone, polyurethane, or grapheme. In certain embodiments, the impeller blades helically circumnavigate the impeller body. The blades may be located at the proximal end of the impeller (FIG. 5A), the distal end of the impeller (FIG. 5B), or along the entire length of the impeller (FIG. 5C). The impeller body may have any suitable shape. For example, in one embodiment, the impeller body has a cylindrical shape along at least a portion of the body. In certain embodiments, the distal end of the impeller body comprises a rounded or pointed tip. Impeller blades can also be continuous or discontinuous along the impeller body.

Figure 6:
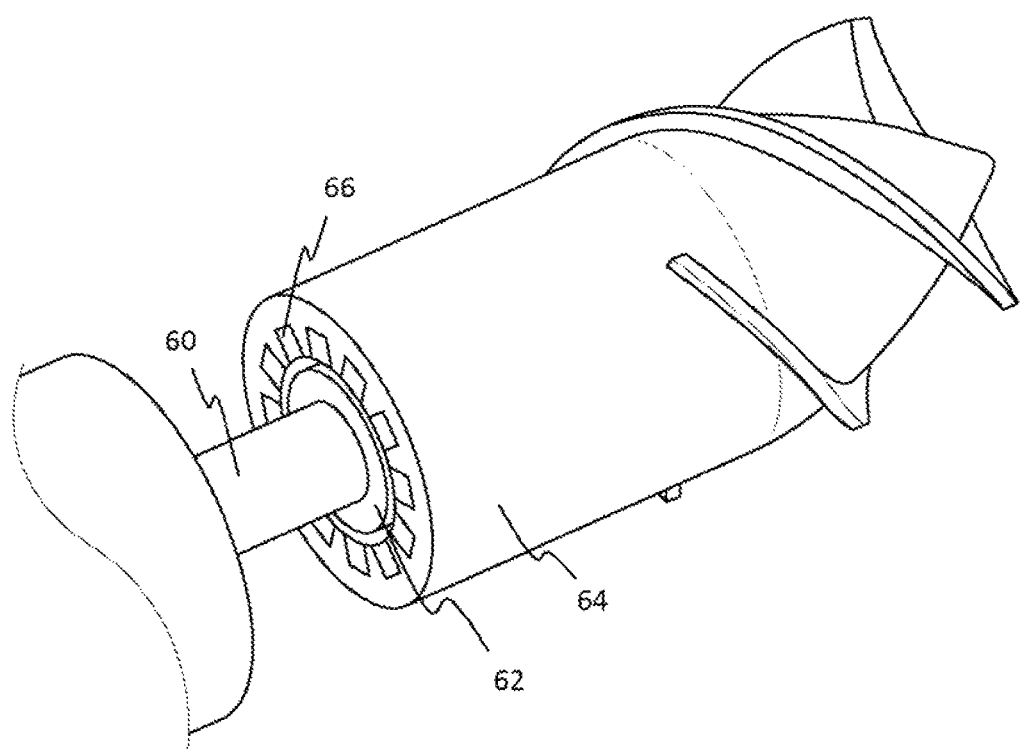
FIG. 6 is a perspective view of an exemplary pump unit having rectangular radially-polarized magnets at a drive shaft magnet to impeller magnet ratio of approximately 1:3.
Figure 7A:
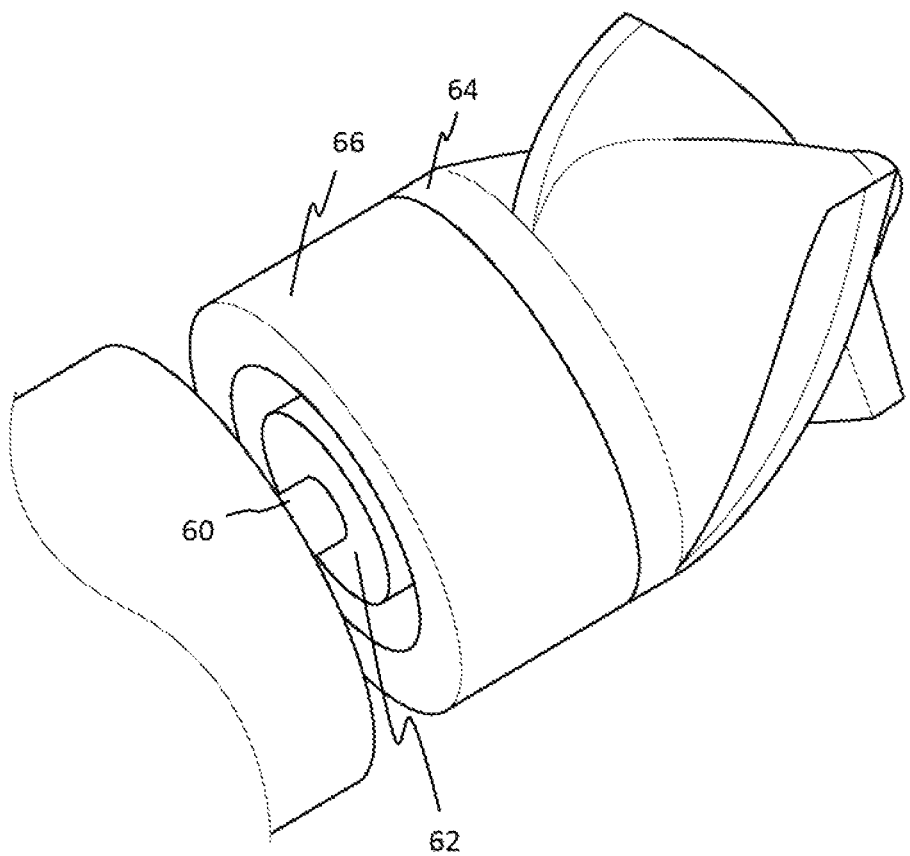
FIGS. 7A and 7B are perspective views of an exemplary pump unit comprising arc-shaped radially-polarized magnets at a drive shaft magnet to impeller magnet ratio of 1:1.
Figure 7B:
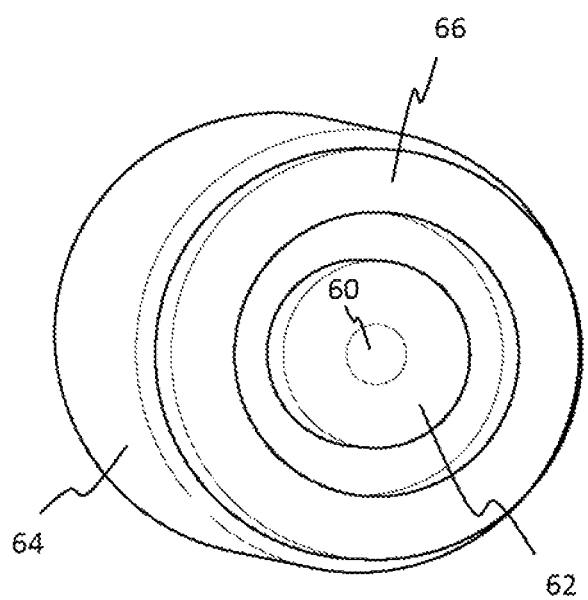

FIGS. 6, 7A and 7B depict a pump unit comprising exemplary impeller and drive shaft magnet configurations. In FIG. 6, a pump unit features multiple rectangular impeller magnets 66 radially polarized and spaced around a proximal portion of the impeller, and a circular ring-shaped drive shaft magnet 62 around the drive shaft, resulting in a drive shaft magnet 62 to impeller magnet 66 ratio of 3:1. In the alternative arrangement shown in FIGS. 7A and 7B, a pump unit comprising contiguous arc-shaped radially polarized impeller magnets 66 and a circular ring-shaped drive shaft magnet 62 form a drive shaft magnet 62 to impeller magnet 66 ratio of 1:1.

In one embodiment, drive shaft is magnetically coupled to a bearingless freely spinning impeller outside of the sealed area. For example, in certain embodiments, the magnetic coupling system provides adequate strength to stabilize the impeller without additional bearings. That is, the strength of the magnetic coupling provides efficient stabilization of the impeller, and thus the use of any bearings to stabilize the impeller is not needed. In one embodiment, the impeller is stabilized at the distal end. For example, the pump unit may comprise a bearing positioned at the distal end of the pump unit that couples to the distal end of the impeller.

The frame of the device may be made of any flexible or elastomeric material, including, but not limited to nitinol, titanium, stainless steel, polyether ether ketone, polyurethane, or grapheme. In a particular embodiment, the frame is constructed of nitinol, a composite of nickel and titanium and is known for its superelasticity and ability to expand to a different shape. For example, in one embodiment, the nitinol frame is configured to expand at a temperature threshold at or near body temperature.

As described above, the frame initially has an elongated narrow shape having a small diameter, which promotes the first compressed conformation of the device within a sheath, where the plurality of pump units are arranged in series (FIG. 1A). As illustrated in FIGS. 1A-1C, upon entering a wider caliber vessel or other body cavity, such as the aorta, and upon deployment from the sheath, the frame expands into a shape having a larger diameter, which promotes the second expanded conformation of the device, where the plurality of pumps are arranged in parallel.

In one embodiment, the device comprises a sheath, configured to surround the frame while the device is in its compressed conformation. The sheath prevents self-expansion of the frame and device when it is first exposed to body temperature but not yet guided to its eventual implantation site. Upon guidance of the device to the implantation site, the sheath may be removed. For example, upon guidance to the aortic arch, which is approximately 3 times wider than that of the femoral artery, the sheath is removed, and the frame is able to expand into the expanded conformation. The sheath may be manufactured from any suitable, biocompatible material.

Each pump unit is connected to the frame using any suitable mechanism. For example, each pump unit may be connected to the frame through an adhesive, permanent bonding, magnetic attraction, locking mechanism or the like. The pump units are positioned and connected to the frame such that upon expansion the pump units rearrange to form a parallel arrangement wherein each pump unit has the same orientation. That is, the pump units are rearranged such that the outlet of each pump unit is similarly positioned. There are several ways in which the pump units can be arranged in the compressed conformation such that they efficiently rearrange to a parallel conformation (see for example FIGS. 8A-12C).

With reference now to the exemplary embodiment shown in FIGS. 8A and 8B, each pump unit is attached to a different radial position along the cylindrical frame 220. The frame 220 is a shape memory material, such as a medical grade alloy, e.g. Nitinol. The frame 220 is generally a spiraled coil that can be stretched or compressed in a sheath 210 to expand each of three pumps 201, 202, 203 into a series configuration. The pumps 201, 202, 203 are each connected to the frame 220 by an attachment component 225, as described herein. The relaxed or unstressed position for the frame 220 is shown in FIG. 8B, where the attachment components 225 are strategically placed so that the pumps 201, 202, 203 organize into a triangular relationship. The different radial positions of the connections may be equidistant from each other (i.e. each connection is separated from an adjacent connection by about 360°/N, where N is the number of pump units in the device). For example, in one embodiment, the device comprises 3 pump units, which are each connected at about 120° apart from one another (for example, see the generic diagram of connection points 701 to the frame 720 shown in FIGS. 12A-12C). The frame can also connect to the pumps at different heights, to facilitate a smooth transition and reorganization to the parallel pump configuration. Thus, upon expansion, each pump unit is able to efficiently rearrange from its serial arrangement into the parallel arrangement without hindrance. However, the present invention is not limited to any particular mechanism for the rearrangement of the pump units into its parallel arrangement. Rather, any mechanism by which the pump units may rearrange from their serial arrangement in the compressed conformation into the parallel arrangement in the expanded conformation is encompassed in the present invention.

Various embodiments of a frame can be employed for reorganizing the pumps from a series back to a parallel position. With reference to the exemplary embodiment of FIGS. 9A-9D, the pumps 301, 302, 303 are attached to a frame 320 that is tensioned towards the middle of the second pump 302, drawing the first pump 301 down and the third pump 303 up, so that all three pumps 301, 302, 303 are in parallel in the relaxed expanded configuration. The frame 320 could tension the pumps 301, 302, 303 by use of a shape memory that has an elastic, springing or biasing property, or by use of a medical grade plastic or rubber, such as silicone, that utilizes a material composition suitable for springing the first 301 and third pump 302 back to a parallel relaxed position. Elastic bands, strips or threads can also be used in a specific weaving or crossing pattern to makeup the frame 320, and to expand and relax the pumps back to their original parallel position. Patterns known in the art, such as those used for flexible stent designs can be utilized.

Figures 10A, 10B:
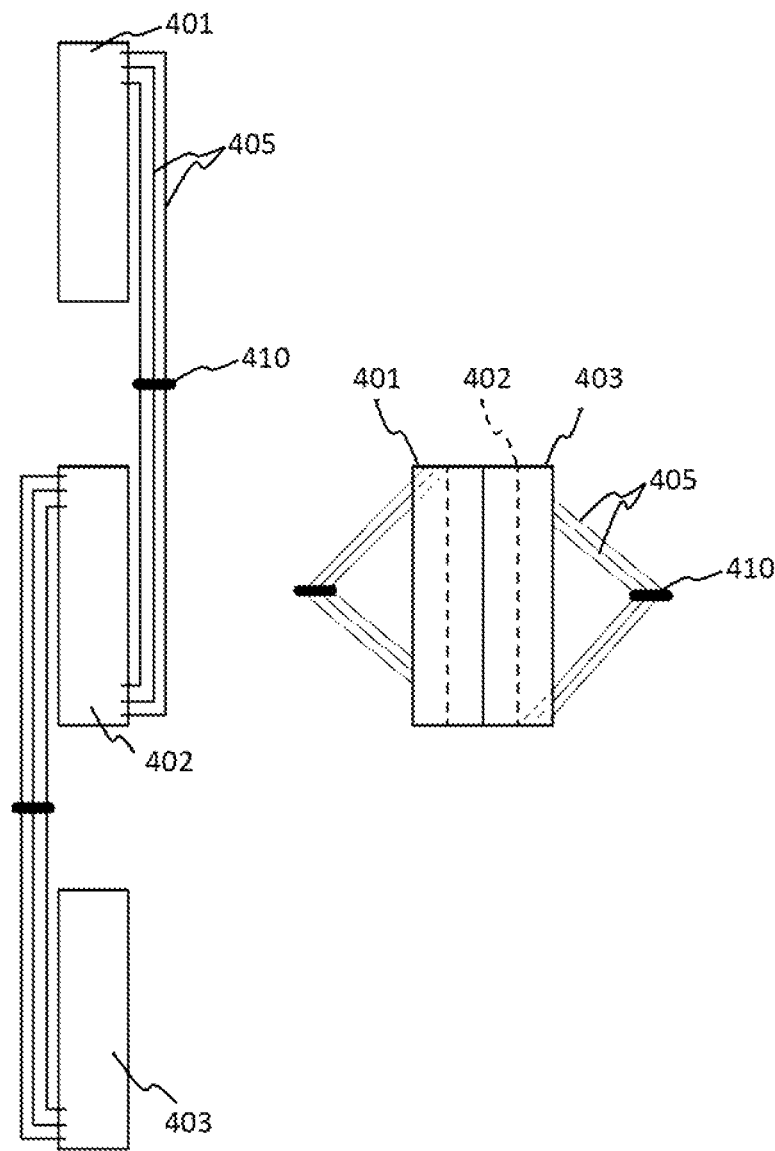
FIGS. 10A and 10B are side views of an exemplary frame suitable to transform the device from its serial to parallel configuration.

As shown in FIGS. 10A and 10B, biasing arms 405 can be attached to a pivot point 410 for reorganizing pumps 401, 402, 403 to a parallel position. The biasing arms can be a number of shape memory materials and alloys known in the art. As shown in FIG. 10A, the biasing arms 405 can be attached to the pumps 401, 402, 403 at opposing points such that the arms 405 in the relaxed position (see FIG. 10B) form anchors at the pivot points 410. In certain embodiments, the pivot points 410 can also feature barbs for anchoring the pumps at a treatment site within the vessel.

Figures 11A, 11B:
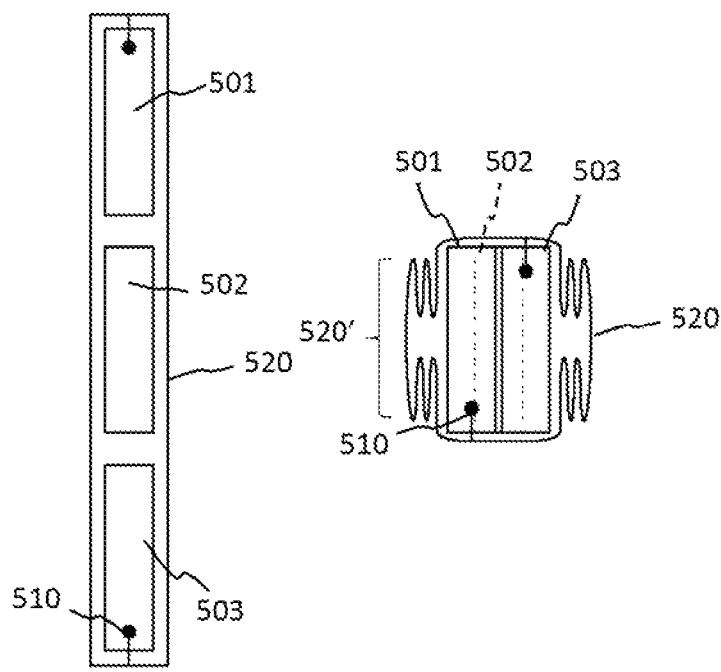
FIGS. 11A and 11B are side views of an exemplary frame suitable to transform the device from its serial to parallel configuration.
Figures 11C, 11D:
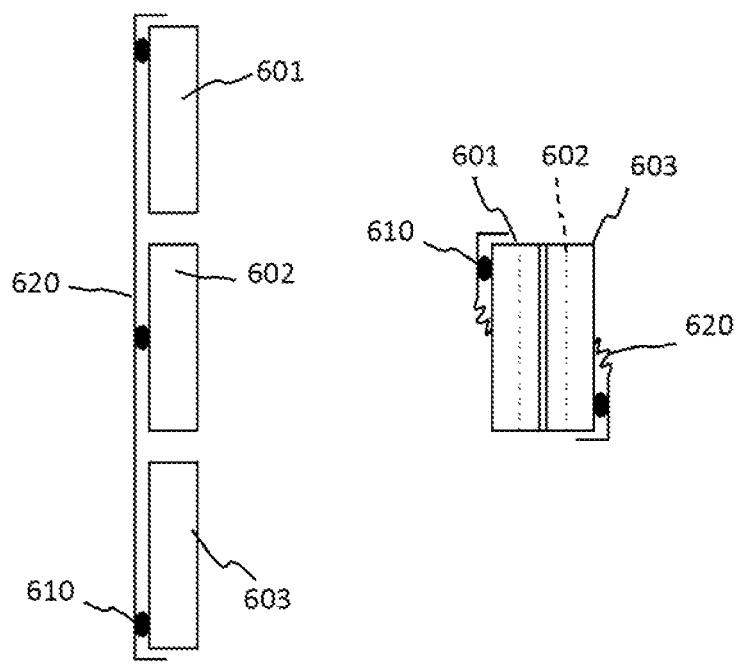
FIG. 11C shows the alternate embodiment frame in a compressed state and FIG. 11D shows the alternate embodiment frame in a relaxed state.
Figures 12A, 12B, 12C:
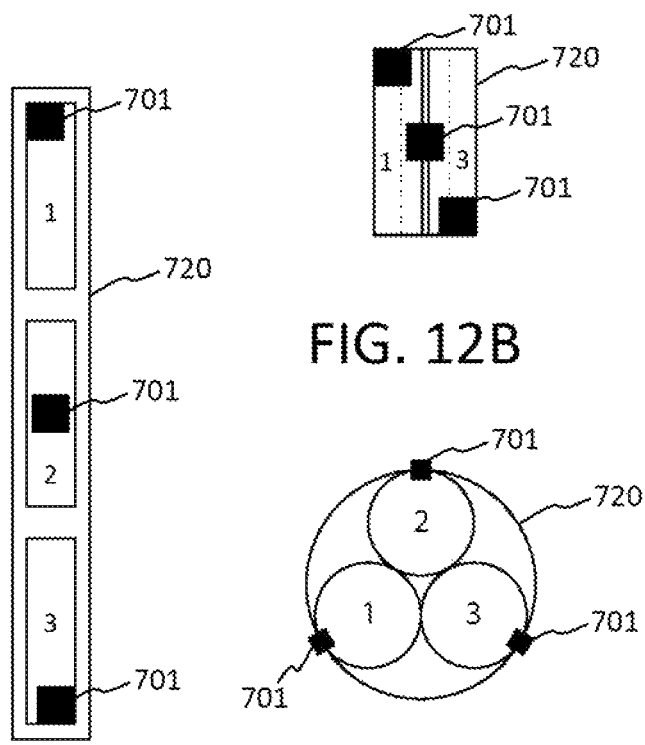
FIGS. 12A-12C depict an exemplary attachment point arrangement for a frame suitable to transform the device from its serial to parallel configuration.

Now with reference to FIGS. 11A and 11B, a frame 520 that is biased to collapse along its sides can also be utilized according to an exemplary embodiment. This collapsing portion 520' can be utilized to the advantage of anchoring the pumps 501, 502, 503 in place during implantation. Attachment points 510 allow the pumps 501, 502, 503 to reorganize in a parallel configuration after being released from a stressed position. In the alternative embodiment shown in FIGS. 11C and 11D, the frame 620 is attached substantially to one side and connects to the pumps 601, 602, 603 at spaced connection points 610. In the relaxed state, the frame 620 reverts to a more compact configuration, and the pumps are reorganized into a parallel configuration (see FIG. 11D).

In one embodiment, one or more of the pump units comprise a power cable operably connected to the motor. In one embodiment, each pump unit comprises its own power cable. In another embodiment, the device comprises a single power cable, which provides power to all of the pump units. In certain embodiments, the power cable can be externalized from the device to outside the body using known techniques. For example, in one embodiment, the power cable can be guided from the device to the right side of heart using a transseptal puncture made using conventional methods. The cable can then be guided through the super vena cava and into the subclavian vein to an area over the right or left side of the chest, where a small incision can be made to retrieve the cable. The device of the invention can be operated with both wired and/or transcutaneous energy transfer (TET) power delivery systems. For the implementation of TET power delivery, a small superficial pocket is created just underneath the skin where a TET coil can be placed and connected to the power cable of the device. Exemplary TET power delivery systems, including systems that wirelessly delivery power to implantable device are described in U.S. patent application Ser. Nos. 13/843,884 and 14/213,256, each of which are incorporated by reference in their entirety.

In certain embodiments, the device of the invention is operably connected to a pump controller. The pump controller may be located exterior to a patient, or implanted within the patient. In certain embodiments, the pump controller delivers and receives signals from the device relating to function of the one or more pump units of the device. For example, the controller may provide signals relating to the control of pump speed, desired flow rate, type of flow produced (pulsatile vs. continuous), and the like. The controller may be directly wired to the device of the invention or may communicate telemetrically to the device.

Figure 13:
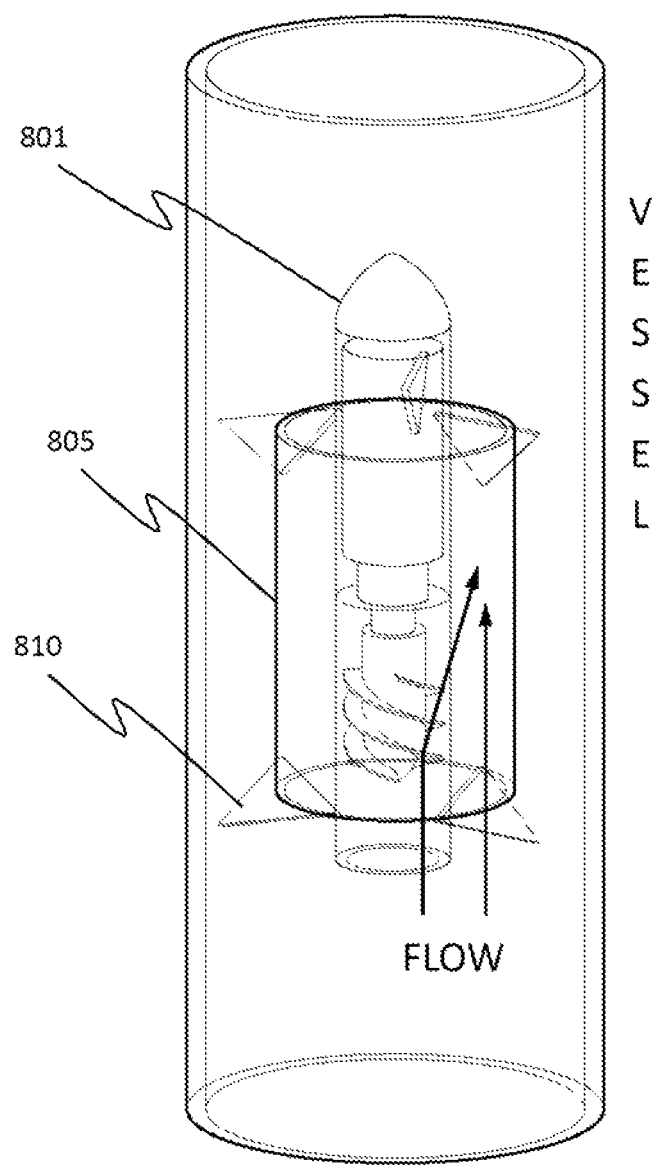
FIG. 13 is a perspective diagram of an exemplary embodiment of the device positioned within a vessel. The device comprises a single pump surrounded by a shell, where the shell increases the flow rate produced by the device according to the Venturi principle.
Figure 14:
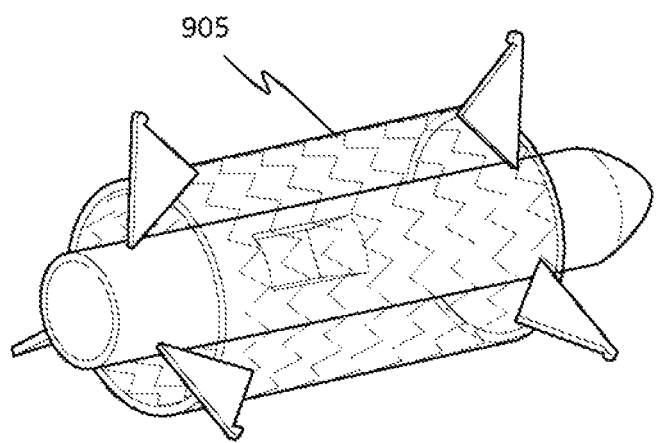
FIG. 14 is an illustration of an exemplary embodiment of the device depicting an elastomeric shell surrounding a single pump.

In one embodiment, the device of the invention comprises a single percutaneously deliverable pump 801, as described elsewhere herein, and a surrounding shell 805, which together is capable of significantly amplifying the flow rate of the pump (see for example FIGS. 13 and 14). With reference to FIG. 13, the shell 805 comprises an exterior wall and an interior wall, forming a shell lumen, wherein the pump 801 is attached within the shell lumen 805. The surrounding shell acts as a flow multiplier via the Venturi principle. Functionally, the shell decreases the cross-sectional area at the fluid outlet, which correspondingly increases the velocity of fluid exiting the pump. This increase in velocity causes a decrease in pressure at the fluid outlet, promoting the additional entrainment of surrounding fluid. In one embodiment, the surrounding shell is made of a frame covered by an elastomer coating. The coating prevents lateral flow of fluid through the frame. The shell may have any suitable geometry which surrounds the outlet of the pump. In certain embodiments, the inner wall of the shell is tapered or may otherwise include various internal diameters along the length of the shell, which may also improve the Venturi effect produced by the shell. The shell is attached to the pump housing using any suitable attachment mechanism. In one embodiment, the device is deliverable in a compressed configuration, where the shell is compressed to the pump housing via a removable outer sheath, as described elsewhere herein. When the outer sheath is removed, the shell expands into its final configuration leaving fluid space between the pump housing and the surrounding interior wall of the shell. In one embodiment, the device comprises one or more anchors 810 positioned along the shell which are used to anchor the device to a desired placement within the body (i.e. blood vessel). For example during placement across the aortic valve, the shell 805 itself may anchor the device at the desired placement site. Accordingly, the shell 905 may also be a stent or stent-like body as shown in FIG. 14, wherein the stent includes the pump within the lumen of the stent as described herein.

This embodiment similarly provides increased flow without the need for the moving component of the pump to be flexible as is the case for prior expandable impeller implementations. While FIGS. 13 and 14, depict this embodiment using a single pump, in certain embodiments, a plurality of pumps, each separately or collectively surrounded by a shell, may be used to amplify the flow rate.

The present invention comprises a method of promoting the movement or flow of a body fluid. The method may be used to aid in the movement or pumping of any body fluid in any location within the body. For example, in certain embodiments, the method comprises delivery and implantation of the device described herein into the aorta or left ventricle to promote pumping of blood from the left ventricle. The device thereby provides long term LVAD function. In one embodiment, the device is delivered through the femoral artery, where it is then guided though the vasculature to the implantation site (e.g. aorta). However, the device may be inserted at any suitable access site.

Notably, the percutaneous delivery method significantly reduces the dangerous risks, extended hospital stay, and corresponding high costs of current long-term LVAD implantation procedures. Current LVADs require an open heart surgery that involves making a long ~20 cm incision through the chest, cracking the ribs, stopping the heart and putting the patient on cardiopulmonary bypass, suturing the LVAD cannulas to the left ventricle and aorta, and then restarting the heart. The procedure takes approximately 4 to 6 hours to complete. Due to the highly invasive nature of the surgery, the patient is then sent to the intensive care unit for a few days and then remains in the hospital for 2 to 4 weeks for recovery. In contrast, the implantation of the present device involves a small approximately 1 cm incision near a percutaneous access site. In certain embodiments, the access site is the femoral artery. The device is then inserted into the femoral artery in its compressed conformation and the operator utilizes x-ray images to guide the device to the eventual implantation site, instead of relying on open visualization. In one embodiment, the device self-expands to the parallel conformation when it reaches the wider regions of the vasculature. For example, in certain embodiments, the dimensions of the vessels used for the delivery of the device help to constrain the device in its compressed conformation. For example, if the device is to be used as an LVAD, the device is guided to the descending aorta, where the device expands into the parallel conformation. The device can then be guided to the ascending aorta or left ventricle. In certain instances, the implantation of the device of the invention can be completed in less than 1 hour and would drastically reduce the recovery process and associated costs. Retrieval of the device can be done using techniques similar to filter retrieval. For instance, forceps or a retrieval hook can be advanced through a catheter or sheath having a retrieval lumen to the implantation site. The forceps or retrieval hook can then grasp or hook onto the frame of the device, and retract the device back into the retrieval lumen. As the device is being dragged backwards into the lumen, the frame will stretch, reorganizing the pumps back into the lower profile serial configuration. In certain embodiments, the hook can twist or spin while retracting to facilitate the serial orientation of the frame and pumps into the retrieval lumen. Likewise, the interior walls of the lumen can be shaped to specially oppose the frame, such that it tends to straighten the pumps back into a serial orientation during retraction into the retrieval lumen.

In one embodiment, the method of the invention is used to aid in the movement or pumping of urine from the bladder. For example, the device of the invention may be inserted into the ureter and guided into the bladder, where the pump units can promote the flow of urine from the bladder.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Design and Development of a Durable, Percutaneous, Wireless Left Ventricular Assist Device Current permanent LVAD devices are hampered by invasiveness associated with implantation, tethered operation and cumbersome peripherals. In spite of miniaturization, delivery and deployment still requires a thoracotomy, conversely percutaneous devices are hampered by durability. Described herein is an endovascularly deployable micro-LVAD with a durable design.

The base unit of the pump comprises of a fully sealed motor and drive shaft magnetically coupled to a bearing less freely spinning impeller. SolidWorks 2013 Computer Aided Design software was utilized to model various configurations of the drive shaft magnet enclosure, impeller magnet enclosure, and pump housing. An Objet 30Pro 3D Printer was used for the rapid prototyping of these components. Various magnetic coupling configurations were compared.

Preliminary in vitro tests of pump performance were performed. The magnetic coupling system provided adequate strength to stabilize the impeller without additional bearings. Several iterations of modeling, rapid prototyping, and testing were performed to achieve progressively smaller footprints. Initial prototypes focused on magnetic coupling of a 20 mm diameter version. Bar and cylindrical magnetic arrangements were tested with axial and radial polarities as well as with continuous and alternating arrangements. This was followed by a 14 mm diameter and finally 8 mm diameter pump, which required the use of alternative housing materials due wall thickness reaching 0.5 mm. The small foot print allows the device to be delivered via the femoral artery or subclavian artery. Further studies will focus on optimizing impeller geometry and outflow design to improve pump performance. By completely sealing the motor, this design eliminates the need for a purge fluid line present in current temporary percutaneous devices. Combining this with a wireless energy transfer system allows for a completely wireless intermediate- to long-term minimally invasive solution.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for promoting the movement of a bodily fluid comprising:
    at least one pump having:
        a sealed motor connected to an impeller, and
        a housing defining a fluid inlet and outlet; and
    a shell having:
        a contiguous and impermeable exterior wall and an interior wall forming a lumen, and one or more anchors positioned on the exterior wall of the shell for displacement from an inner-vessel wall and configured for attachment of the device to a desired implantation site;
    wherein the pump is attached to the shell such that at least a portion of the pump and the fluid outlet is positioned within the lumen of the shell, and wherein the shell is configured to increase a velocity of fluid exiting the shell and generate a venturi effect.

2. The device of claim 1, wherein the shell is compressible around at least a portion of the pump.

3. The device of claim 2, further comprising a removable sheath that surrounds the shell and pump when the shell is compressed, such that when the shell and pump are released from the sheath, the shell expands to its relaxed state.

4. The device of claim 1, wherein the shell comprises a frame covered by a solid elastomeric material.

5. The device of claim 1, wherein the inner wall forming the lumen of the shell is tapered.

6. The device of claim 1, wherein a fluid outlet of the pump is positioned within the shell lumen between the sealed motor and the impeller.

7. The device of claim 1, wherein at least one of the interior and exterior wall of the shell is contiguous.

8. A device for promoting the movement of a bodily fluid comprising:

at least one pump comprising:

a sealed motor connected to an impeller, and a housing defining a fluid inlet and outlet; and a shell comprising:

a contiguous and impermeable wall forming a lumen, and one or more anchors positioned on the exterior wall of the shell for displacement from an inner-vessel wall and configured for attachment of the device to a desired implantation site;

wherein the pump is positioned within the shell such that at least a portion of the pump and the fluid outlet is positioned within the lumen of the shell.

9. The device of claim 8, wherein the shell is configured to increase a velocity of fluid exiting the shell and generate a venturi effect.

10. A device for promoting the movement of a bodily fluid through a target vessel comprising:

at least one pump comprising:

a sealed motor connected to an impeller, and a housing defining a fluid inlet and outlet; and a shell comprising:

a contiguous and impermeable wall forming a lumen, and one or more anchors positioned on the exterior wall of the shell for displacement from an inner-vessel wall and configured for attachment of the device to a desired implantation site;

wherein the pump is positioned within the shell such that at least a portion of the pump and the fluid outlet is positioned within the lumen of the shell, and wherein an inner diameter of the shell is less than an inner diameter of the target vessel.

11. The device of claim 10, wherein the shell is configured to increase a velocity of fluid exiting the shell and generate a venturi effect.

12. The device of claim 10, wherein the wall of the shell is contiguous.

\* \* \* \* \*